United States Patent

Prost et al.

[11] 4,332,805
[45] Jun. 1, 1982

[54] DECAHYDROQUINOLINOL DERIVATIVES AND METHODS OF TREATING CARDIAC ARRYTHMIAS OR INDUCING LOCAL ANAESTHESIA WITH THEM

[75] Inventors: Maurice Prost, Brussels; Michel de Claviere, Vilvoorde, both of Belgium

[73] Assignee: Sanofi, Paris, France

[21] Appl. No.: 184,129

[22] Filed: Sep. 4, 1980

[30] Foreign Application Priority Data

Sep. 19, 1979 [FR] France ............................... 79 23289

[51] Int. Cl.³ ..................... A61K 31/47; C07D 215/22
[52] U.S. Cl. ..................................... 424/258; 546/153
[58] Field of Search ......................... 546/153; 424/258

[56] References Cited

U.S. PATENT DOCUMENTS 3,882,129  5/1975  Prost et al. ..................... 546/153
4,173,636  11/1979  Prost ................................ 424/258

*Primary Examiner*—Anton H. Sutto
*Assistant Examiner*—Diana G. Rivers

[57] ABSTRACT

Decahydroquinolinol derivatives corresponding to the general formula:

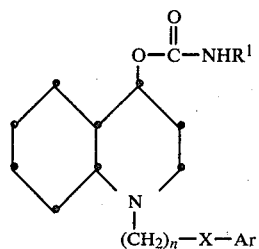

and pharmaceutically acceptable acid addition salts thereof, in which $R^1$ represents hydrogen, a methyl, ethyl, n-propyl, n-butyl or phenyl radical or a phenyl radical having one substituent or two identical or different substituents selected from chlorine, bromine atoms and a methyl group.

Ar represents a phenyl or naphthyl radical or a phenyl radical having one substituent or two identical or different substituents selected from fluorine, chlorine and bromine atoms and methyl, methoxy, acetyl and cyano groups, X represents oxygen or sulfur, n represents 2 or 3.

They are useful as antiarrhthmic and local anaesthetic agents.

17 Claims, No Drawings

DECAHYDROQUINOLINOL DERIVATIVES AND METHODS OF TREATING CARDIAC ARRYTHMIAS OR INDUCING LOCAL ANAESTHESIA WITH THEM

This invention relates to novel heterocyclic compounds and more particularly to novel decahydroquinolinol derivatives as well as to a process for preparing the same.

The decahydroquinolinol derivatives of the invention can be represented by the general formula:

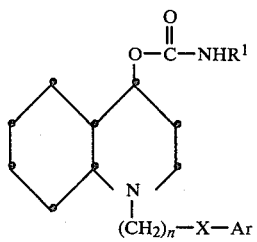
I in which

R$^1$ represents hydrogen, a methyl, ethyl, n-propyl, n-butyl or phenyl radical or a phenyl radical having one substituent or two identical or different substituents selected from chlorine, bromine atoms and a methyl group.

Ar represents a phenyl or naphthyl radical or a phenyl radical having one substituent or two identical or different substituents selected from fluorine, chlorine and bromine atoms and methyl, methoxy, acetyl and cyano groups, X represents oxygen or sulphur, n represents 2 or 3.

The present invention also relates to the pharmaceutically acceptable acid addition salts of the derivatives of formula I, for instance the hydrochloride or methanesulphonate.

The compounds of formula I possess in the 4-position of the decahydroquinoline ring, a carbamoyloxy radical which can present an axial or equatorial configuration.

The invention relates to axial and equatorial epimers and also to mixtures of these epimers.

The decahydroquinolinol derivatives of the invention have been found to possess potent pharmacological properties likely to render them particularly useful in the treatment of cardiac arrhythmias of various origins and in particular in the treatment of arrhythmias due to myocardial infarction.

Furthermore, the compounds of the invention have been found to possess very valuable topical anaesthetic properties.

Another object of the present invention is therefore concerned with novel medicaments useful more particularly as local anaesthetic agents and in the treatment of cardiac arrhythmias of various origins, medicaments constituted by a decahydroquinolinol derivative of formula I or by a pharmaceutically acceptable acid addition salt thereof.

Another object of the present invention relates to pharmaceutical or veterinary compositions comprising as essential active ingredient at least one decahydroquinolinol derivative of formula I or a pharmaceutically acceptable acid addition salt of this derivative, in association with a pharmaceutical carrier or excipient.

Yet, another object of the invention relates to a process for preparing pharmaceutical or veterinary compositions, process comprising the association of a decahydroquinolinol derivative of formula I or a pharmaceutically acceptable acid addition salt thereof with an appropriate pharmaceutical carrier or excipient.

Furthermore, the invention is concerned with a method of treating cardiac arrhythmias of various origins and in particular a method of treating arrhythmias due to myocardial infarction in a host in need of such treatment, which method comprises the administration to said host of an effective dose of at least one decahydroquinolinol of formula I or a pharmaceutically acceptable acid addition salt thereof.

The daily effective dose will be, for instance, from 100 to 200 mg by oral route to a human being weighing 60 kgs.

Similarly, another object of the invention is to provide a method of inducing local anaesthesia in a host in need thereof, which method comprises the administration to said host of an effective dose of at least one compound of formula I or a pharmaceutically acceptable acid addition salt of such compound.

The compounds of formula I can each be prepared starting from 4-hydroxy-trans-decahydroquinoline.

This compound is first reacted with a halogenated compound of general formula:

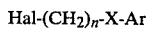
II wherein Hal represents a chlorine, bromine or iodine atom and n, X and Ar have the same meaning as above, to provide the N-substituted 4-hydroxy-trans-decahydroquinoline of general formula:

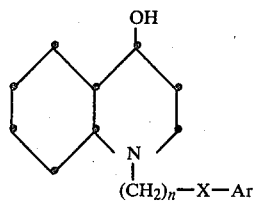
III in which n, X and Ar have the same meaning as above.

This reaction is carried out preferably in an alcoholic medium, for example butanol, or in a ketonic medium, for example methyl ethyl ketone, and in the presence of an acid acceptor preferably an alkali metal carbonate, for example potassium carbonate, sodium carbonate or sodium hydrogenocarbonate.

The reaction which can be accelerated by means of small amounts of potassium iodide is preferably performed at the reflux temperature of the solvent.

The N-substituted 4-hydroxy-trans-decahydroquinoline of formula III is then reacted in an inert organic solvent such as, for example, benzene, toluene or dichloromethane, and at room-temperature, with a compound of general formula:

IV in which R$^2$ represents a chlorine atom or a phenoxy radical to obtain a carbonyloxy derivative of general formula:

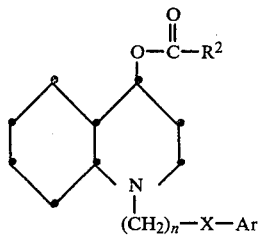

in which n, X, $R^2$ and Ar have the same meaning as above, this carbonyloxy derivative being subsequently condensed with ammonia or a primary amine of general formula:

$$H_2N\text{-}R^1 \qquad\qquad VI$$

in which $R^1$ has the same meaning as above, preferably in an inert solvent, for instance toluene or dichloromethane or a mixture of these two solvents, and at room-temperature to form the corresponding carbamic ester of decahydroquinolinol of formula I in free base form.

The pharmaceutically acceptable acid addition salts of the compounds of formula I can be obtained, in a classical manner, by reacting the corresponding compound of formula I in free base form with an organic acid such as, for example, methanesulphonic acid, or an inorganic acid such as, for example, hydrochloric acid.

The halogenated compounds of formula II can be prepared in accordance with the method described by Ch. K. GROGAN et al in J. Med. Chem. 1965, 8, 62 or by other known procedures.

With respect to the starting 4-hydroxy-trans-decahydroquinoline, this compound is known and can be prepared by reducing 4-oxo-trans-decahydroquinoline in accordance with the method described for instance in Bull. Acad. Sci. U.S.S.R., 1962, 1599.

This method provides a mixture of axial and equatorial epimers at the hydroxyl-position. These epimers in separated form are described together with their preparation and identification by M. PROST et al in Eur. J. Med. Chem. 1976, 11 (4) pp. 337–342.

Thus, the processes hereabove described for preparing the derivatives of formula I starting from 4-hydroxy-trans-decahydroquinoline can be applied either to the axial epimer or to the equatorial epimer of 4-hydroxy-trans-decahydroquinoline to provide the corresponding epimers of formula I.

Similarly, the processes in question can be carried out with a mixture of axial and equatorial epimers of 4-hydroxy-trans-decahydroquinoline obtained, for instance, by reduction of 4-oxo-trans-decahydroquinoline, in order to prepare the compounds of formula I in the form of a mixture of axial and equatorial epimers.

Compounds with a chemical structure similar to that of the compounds of formula I hereabove and presenting antiarrhythmic properties are already known having been published in U.S. Pat. No. 3,882,129.

Such compounds are characterized by a 4-(4-fluoro-phenyl)-4-oxo-butyl chain in the 1-position of the decahydroquinoline ring.

However, the antiarrhythmic properties of the decahydroquinoline derivatives in question manifest themselves only by venous route. It has been, in fact, observed that this activity of these compounds concerned is very weak by oral route rendering them without any value as antiarrhythmic agents when administered by this route.

Furthermore, the antiarrhythmic derivatives of the U.S. patent in question are likely to provok, on the one hand, considerable drops in arterial pressure by reason of their powerful antiadrenergic activity and, on the other, a reduction in cardiac output due to the depressive effect that they exert on the contractility of the myocardium.

Finally they depress central nervous activity and are, in particular, sedative agents.

The use of such products is thus limited by these undesirable side-effects and severe monitoring of the patient is therefore required.

It has now been found quite unexpectedly that a slight alteration of the 4-(4-fluoro-phenyl)-4-oxo-butyl chain in question i.e. the replacement of the carbonyl function by an ether-oxide function provides novel decahydroquinolinol derivatives which present marked local anaesthetic properties leading to cardiac electrophysiological alterations and valuable antiarrhythmic effects.

These antiarrhythmic effects are consequent more particularly upon a mechanism of action which is entirely different from that of the derivatives of the U.S. patent in question.

Furthermore, pharmacological tests have shown that the compounds of the invention are much more active, by oral route, that the decahydroquinolinol derivatives of the U.S. patent cited above.

Therefore, the possibilities of use of the derivatives of the invention in the antiarrhythmic field will be wider than those offered by the derivatives of U.S. Pat. No. 3,882,129; thus, it will be possible to use the compounds of the invention for instance in ambulatory treatment where the derivatives of the state of the art will of course be of little or no value.

Amongst the compounds of the present invention, the following products have shown the best potential antiarrhythmic properties:

4-Carbamoyloxy-1-[3-(4-fluoro-phenoxy)-propyl]-trans-decahydroquinoline (axial form) referred to, hereunder, as Compound A and 4-[(3-Chloro-4-methyl-phenyl)-carbamoyloxy]-1-[3-(4-fluoro-phenoxy)propyl]-trans-decahydroquinoline (equatorial form)

these derivatives being in the form of a free base or of a pharmaceutically acceptable acid addition salt, such as the hydrochloride or methanesulfonate.

Pharmacological tests carried out more particularly with Compound A have shown that this compound is endowed with the entire range of properties desired for the treatment of arrhythmias of various origins.

Thus, it has been found that Compound A presents a markedly polyvalent antiarrhythmic activity which manifests itself both at the auricular and ventricular levels according to the different types of cardiac arrhythmias experimentally induced. For instance, Compound A is active at a dose as low as 1 to 2.5 mg/kg by intravenous route in the dog against ventricular arrhythmias induced by epinephrine, baryum chloride or ouabain.

Compound A also provides protection against ventricular fibrillation provoked by chloroform or by calcium chloride and against auricular fibrillation provoked by acetylcholine.

Furthermore, Compound A is neither a hypotensive agent since its mechanism of action does not result from antiadrenergic properties nor is it a depressant of myocardial contractility. It does not induce arrhythmia at toxic doses either since the arrhythmia-inducing dose is 80.6±6.0 mg/kg and the lethal dose is 84.1±7.1 mg/kg in continuous venous perfusion in the anaesthetized dog.

Finally, Compound A does not affect mental and sensory acuity since it does not modify motor activity in the mouse.

In the light of these different properties, the compounds of the invention and in particular Compound A constitute a valuable source of substances potentially useful for the treatment of arrhythmias of various origins, for instance for the treatment of auricular fibrillation in particular of parasympathetic origin.

Moreover, the compounds of the invention can be used to advantage in the treatment, for example, of post-infarction arrhythmias which would consequently render them of undoubted value in the prevention of sudden death through ventricular fibrillation following myocardial infarction. Amongst the most effective agents used in the treatment of post-infarction arrhythmias, lidocaine is probably one of the most widely utilized. However, this compound is only useful by venous route as an antiarrhythmic agent since its plasmatic half-life in humans is very short, being in the region of 15 minutes.

Although it is consequently difficult to exceed toxic doses with this product, the fact remains that it is by no means easy to regulate the rate of perfusion of this substance in order to stabilize the plasma level.

The compounds of the invention do not present this disadvantage because unlike lidocaine, they are active by oral route, as indicated above, and have a longer duration of action.

This double advantage constitutes a considerable advance on the pharmacological plane in comparison with lidocaine. The plasma level of the antiarrhythmic agent according to the invention will be more easily stabilized over a period of time and ambulatory treatment will become possible thus eliminating the need to hospitalize the patient.

Results obtained during the pharmacological study of the compounds of the invention are given hereunder:

A. Antiarrhythmic properties

These properties have been demonstrated using the LAWSON test (J. Pharmac. Exp. Therap. 1968, 160 (1) 22-31).

The arrhythmia was induced, in this test, by inhalation of chloroform until breathing stopped.

For each dose of the substance to be studied, batches of 10 female mice, each of about 20 g, were used. These mice had been fasting for 18 hours before the test. A batch of 10 animals was used as control group.

A dose of the compound to be studied was first administered by intragastric route except to the controls which only received the solvent used with the compound in question. Thirty minutes later, the animals were placed under a dome-shaped receptacle containing a high concentration of chloroform obtained by means of a strongly impregnated pad.

The animals were removed when totally asphyxiated (about 2 minutes later), the thorax was rapidly opened and the ventricular rhythm observed. The dose of the compound under study which protected 50% of the animals against ventricular fibrillation was then determined.

This protective dose is expressed as $AD_{50}$ in mg/kg in the following Table. The compounds of formula I were used in the form of a pharmaceutically acceptable acid addition salt, more particularly in hydrochloride form, and were compared to lidocaine.

TABLE

| $R^1$ | n | X | Ar | Stereochemistry of the OCO—$NHR^1$ | $AD_{50}$ (mg/kg) |
|---|---|---|---|---|---|
| hydrogen | 3 | O | 4-fluoro-phenyl | axial | 45 |
| methyl | 3 | O | 4-fluoro-phenyl | axial | 55 |
| ethyl | 3 | O | 4-fluoro-phenyl | axial | 50 |
| n-propyl | 3 | O | 4-fluoro-phenyl | axial | 80 |
| n-butyl | 3 | O | 4-fluoro-phenyl | axial | 50 |
| phenyl | 3 | O | 4-fluoro-phenyl | axial | >100 |
| 4-bromo-phenyl | 3 | O | 4-fluoro-phenyl | axial | 150 |
| 3-chloro-4-methyl-phenyl | 3 | O | 4-fluoro-phenyl | axial | >100 |
| hydrogen | 3 | O | phenyl | axial | >100 |
| hydrogen | 3 | O | 4-bromo-phenyl | axial | 65 |
| hydrogen | 3 | O | 4-chloro-phenyl | axial | >100 |
| hydrogen | 3 | O | 4-methyl-phenyl | axial | >100 |
| hydrogen | 3 | O | 4-methoxy-phenyl | axial | >100 |
| hydrogen | 3 | O | 4-acetyl-phenyl | axial | >100 |
| hydrogen | 3 | O | 4-cyano-phenyl | axial | 30 |
| hydrogen | 3 | O | 2-methoxy-4-acetyl phenyl | axial | >100 |
| 4-bromo-phenyl | 3 | O | 2-methoxy-4 acetyl-phenyl | axial | >100 |
| hydrogen | 3 | O | 1-naphthyl | axial | >100 |
| hydrogen | 3 | O | 2-naphthyl | axial | >100 |
| hydrogen | 2 | O | 4-fluoro-phenyl | axial | >100 |
| hydrogen | 2 | O | 4-bromo-phenyl | axial | 90 |
| hydrogen | 2 | O | 2,6-dichloro-phenyl | axial | 50 |
| hydrogen | 2 | O | 2-methoxy-phenyl | axial | 75 |
| hydrogen | 2 | O | 1-naphthyl | axial | 75 |
| hydrogen | 2 | O | 2-naphthyl | axial | 50 |
| hydrogen | 3 | S | 4-fluoro-phenyl | axial | >100 |
| hydrogen | 3 | O | 4-fluoro-phenyl | equatorial | 45 |
| 4-bromo-phenyl | 3 | O | 4-fluoro-phenyl | equatorial | 120 |
| 3-chloro-4 methyl-phenyl | 3 | O | 4-fluoro-phenyl | equatorial | 30 |
| lidocaine | | | | | 35 |

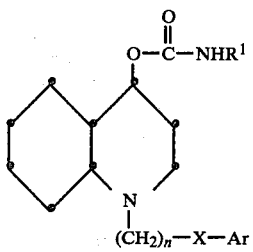

Another comparative test was performed under the same conditions with several compounds included within the scope of U.S. Pat. No. 3,882,129 at the single dose of 100 mg/kg by intragastric route.

The following results were obtained which are expressed in percentage of protection obtained against the arrhythmic effect at the studied dose:

| R¹ | n | X | Ar | Stereochemistry of OCO—NHR¹ | % of protection |
|---|---|---|---|---|---|
| hydrogen | 3 | OCO | 4-fluoro-phenyl | axial | 35 |
| methyl | 3 | OCO | 4-fluoro-phenyl | axial | 35 |
| ethyl | 3 | OCO | 4-fluoro-phenyl | axial | 30 |
| n-propyl | 3 | OCO | 4-fluoro-phenyl | axial | 0 |
| 4-bromo-phenyl | 3 | OCO | 4-fluoro-phenyl | axial | 0 |
| hydrogen | 3 | OCO | 4-fluoro-phenyl | equatorial | 35 |

These results clearly show that the fact of replacing the carbonyl function by an ether-oxide function in the chain attached in the 1-position of the decahydroquinoline ring considerably increases antiarrhythmic activity by intragastric route.

Although, in this test, most of the compounds of the invention are less active than lidocaine 30 minutes after administration, the fact remains that their duration of action is much longer. Thus, 75 mg/kg of Compound A or 75 mg/kg of lidocaine, by intragastric route in mice gave the following results:

| Time after administration (in minutes) | % of protection | |
|---|---|---|
| | Compound A | Lidocaine |
| 30 | 80 | 95 |
| 60 | 65 | 65 |
| 120 | 60 | 25 |
| 180 | 45 | — |
| 240 | 30 | — |

B. Antiadrenergic and sedative properties

Tests carried out with Compound A have shown that a dose of 50 mg/kg administered by intragastric route to mice 30 minutes before the intravenous injection of 3 mg/kg of epinephrine gave no protection against the toxic effects of this catecholamine.

Similarly, an intragastric dose of 50 mg/kg of Compound A administered to mice provoked no depression of spontaneous motility 30 minutes later. These results prove that Compound A is neither sedative nor antiadrenergic at antiarrhythmic doses.

C. Local anaesthetic properties

These properties were demonstrated in the guinea-pig using the technique of CHANCE and LOBSTEIN which consists in placing a drop of a solution of the compound to be studied in the eye of the animal and verifying, at different times after administration, whether or not the eyelid closes after the cornea has been touched.

In this way, the percentage of locally anaesthetized animals were determined with respect to both the dose of compound given and the length of time elapsing after administration.

It was observed that a solution of Compound A at the concentration of 0.1% produced local anaesthesia in 58% of the animals 5 minutes after administration while an identical concentration of lidocaine 5 minutes after administration resulted in local anaesthesia in only 26% of the guinea-pigs.

Furthermore, a solution of lidocaine at the concentration of 0.5% protected only 35% of the animals 15 minutes after administration while an identical dose of Compound A still protected 35% of the guinea-pigs 30 minutes after administration.

These results show that Compound A is more active than lidocaine as a local anaesthetizing agent and exerts its effects over a longer period of time.

D. Toxicity

Acute toxicity tests were undertaken with Compound A on mice and rats. By intravenous and intragastric routes, the $LD_{50}$ of Compound A, namely the dose required to kill 50% of the animals, was 42.5 mg/kg and 750 mg/kg respectively in mice. In rats, by intravenous and intragastric routes, the $LD_{50}$ was 47 mg/kg and more than 2000 mg/kg respectively.

In comparison with Compound A, lidocaine was found to be more toxic, the $LD_{50}$ by intravenous route being 12.5 mg/kg and by intragastric route 360 mg/kg in the rat.

Moreover, Compound A presents a good safety margin between its effective antiarrhythmic dose and its convulsant dose as shown in the following Table:

| | Dose in mg/kg | |
|---|---|---|
| | Antiarrhythmic | Convulsant |
| Mice (per os) | 45 (LAWSON $AD_{50}$ test) | 300 to 400 ($AD_0$) |
| Dog (i.v.) | 1 to 2.5 (anaesthetized dog) | 6 to 10 (conscious dog) |

It will be appreciated that for therapeutic use the compound of the invention will normally be administered in the form of a pharmaceutical or veterinary composition, which will be in a dosage unit form appropriate to the desired mode of administration.

Thus the pharmaceutical or veterinary composition may be in a dosage unit form suitable for oral administration, for example a coated or uncoated tablet, a hard- or soft-gelatin capsule, a packaged powder or a discrete amount of a suspension or a syrup. The composition may alternatively take the form of a suppository for rectal administration, of a solution or suspension for parenteral administration or of a cream, an ointment, a lotion or a gel for topical administration.

Irrespective of the form the composition takes, the parmaceutical or veterinary composition of the invention will normally be prepared by associating at least one of the compounds of formula I or a pharmaceutically acceptable acid addition salt thereof with an appropriate pharmaceutical carrier or excipient therefor, for example, one or more of the following substances: distilled water, benzyl alcohol, milk sugar, starches, talc, magnesium stearate, polyvinylpyrrolidone monopotassium phosphate, alginic acid, colloidal silica, polyethyleneglycol or flavouring agents.

The preparation of the compounds of the invention as well as of a therapeutic composition containing them are illustrated by the non-limitative Examples which follow:

EXAMPLE 1

4-Carbamoyloxy-1-[3-(4-fluoro-phenoxy)-propyl]-trans-decahydroquinoline (axial form) and its hydrochloride (a)

1-[3-(4-Fluoro-phenoxy)-propyl]-4-hydroxy-trans-decahydroquinoline (axial form) and its hydrochloride A solution of 12.5 g (0.08 mol) of 4-hydroxy-trans-decahydroquinoline (axial form) and 16.6 g (0.088 mol) of 1-(3-chloro-propoxy)-4-fluorobenzene in 120 ml of 1-butanol was refluxed for 48 hours in the presence of 9 g of sodium hydrogenocarbonate.

The water formed in the course of the reaction was eliminated by azeotropic distillation. After cooling, the salts were filtered out, the filter was washed with a little 1-butanol and the filtrate was evaporated to dryness.

The residue was taken up in 150 ml of diethyl ether and the solution so formed was acidified with 10%-hydrochloric acid.

The aqueous phase was decanted and made alkaline with 10%-sodium hydroxide.

After extracting again with diethyl ether, the ethereal phase was washed with water. After drying on sodium sulphate and filtration the solvent was eliminated. The residue obtained after evaporation crystallized in the presence of 75 ml of n-hexane. The crystals were filtered out and the filter was washed with a little n-hexane. In this manner were obtained 18 g of 1-[3-(4-fluoro-phenoxy)-propyl]-4-hydroxy-trans-decahydroquinoline (axial form) in the form of a free base.

Yield: 65%

M.P.: 95±1° C.

The base so obtained was dissolved in 2-propanol and a stoechiometric amount of gaseous hydrochloric acid in 2-propanol was added. After elimination of the solvent, the residue was recrystallized from an ethyl acetate/methanol mixture.

In this manner, 1-[3-(4-fluoro-phenoxy)-propyl]-4-hydroxy-trans-decahydroquinoline hydrochloride (axial form) was obtained.

M.P. 167°-170° C.

Using the appropriate starting-products and the process hereabove described, the following compounds were prepared:

For each compound of axial form, the solvent of recrystallization was an ethyl acetate/methanol mixture.

| Compound | M.P. °C. |
| --- | --- |
| 4-Hydroxy-1-(3-phenoxy-propyl)-trans-decahydroquinoline hydrochloride (axial form) | 170 ± 1 |
| 1-[3-(4-Bromo-phenoxy)-propyl]-4-hydroxy-trans-decahydroquinoline hydrochloride (axial form) | 182 ± 1 |
| 1-[3-(4-Chloro-phenoxy)-propyl]-4-hydroxy-trans-decahydroquinoline hydrochloride (axial form) | 167 ± 1 |
| 4-Hydroxy-1-[3-(4-methoxy-phenoxy)-propyl]-trans-decahydroquinoline hydrochloride (axial form) | 136 ± 1 |
| 1-[3-(4-Cyano-phenoxy)-propyl]-4-hydroxy-trans-decahydroquinoline hydrochloride (axial form) | 162 ± 1 |
| 4-Hydroxy-1-[3-(1-naphthyloxy)-propyl]-trans-decahydroquinoline hydrochloride (axial form) | 154 ± 1 |
| 4-Hydroxy-1-[3-(2-naphthyloxy)-propyl]-trans-decahydroquinoline hydrochloride (axial form) | 187 ± 1 |
| 1-[3-(4-Acetyl-2-methoxy-phenoxy)-propyl]-4-hydroxy-trans-decahydroquinoline hydrochloride (axial form) | 170 ± 1 |
| 1-[3-(4-fluoro-phenylthio)-propyl]-4-hydroxy-trans-decahydroquinoline hydrochloride (axial form) | 157 ± 1 |
| 1-[2-(2-Cyano-phenoxy)-ethyl]-trans-decahydroquinoline hydrochloride (axial form) | 212 ± 1 |
| 4-Hydroxy-1[2-(1-naphthyloxy)-ethyl]-trans-decahydroquinoline hydrochloride (axial form) | 246 ± 1 |
| 4-Hydroxy-1-[2-(2-naphthyloxy)-ethyl]-trans-decahydroquinoline hydrochloride (axial form) | 188 ± 1 |
| 1-[3-(4-Fluoro-phenoxy)-propyl]-4-hydroxy-trans-decahydroquinoline hydrochloride (equatorial form) | 99 ± 1 (cyclohexane) |

(b)

4-Carbamoyloxy-1-[3-(4-fluoro-phenoxy)-propyl]-trans-decahydroquinoline (axial form) and its hydrochloride At a temperature of 0° to 5° C., a solution of 200 g of phosgene in 1 l of anhydrous toluene was prepared. After that was added between 0° and −10° C. a solution of 278 g (0.9 mol) of 1-[3-(4-fluoro-phenoxy)-propyl]-4-hydroxy-trans-decahydroquinoline (axial form) in 1.5 l of dichloromethane. When the operation of addition was terminated, the reaction mixture was maintained under stirring at a temperature of 20° to 22° C. for 2 days. The excess phosgene was eliminated by keeping the reaction medium for 2 hours under vacuum by means of a water pump while maintaining the temperature of 20° to 25° C. by gently heating.

Incipient crystallization was observed and the volume was adjusted again with dichloromethane.

The reaction medium was cooled to about 5° C. and saturated with ammonia. The mixture was maintained for 48 hours under stirring and then an additional amount of concentrated ammonia solution i.e. 1.2 l was added. The medium was stirred for a further 24 hours at room-temperature (21±2° C.) and the aqueous phase was decanted out.

The solvent of the organic phase was evaporated off and the solidified residue was reconverted to a paste in 1 l of hexane. The crystals of 4-carbamoyloxy-1-[3-(4-fluoro-phenoxy)-propyl]-trans-decahydroquinoline (axial form) in free base form so obtained were filtered out.

M.P.: 116±1° C.

After drying, the base so obtained was dissolved in 2 l of ethyl acetate and the hydrochloride was prepared by adding a stoechiometric amount of gaseous hydrochloric acid dissolved in 2-propanol.

The desired hydrochloride precipitated. It was filtered out and the filter was washed with acetone. After drying, this product was recrystallized from a 6/4 ethyl acetate/methanol mixture and then dried.

In this manner, 278.5 g of 4-carbamoyloxy-1-[3-(4-fluoro-phenoxy)-propyl]-trans-decahydroquinoline hydrochloride (axial form) were obtained.

Yield: 80%

M.P.: 238±1° C.

Starting from the appropriate products and using the process described above, the compounds hereunder were prepared:

| Compound | M.P. °C. |
| --- | --- |
| 4-Carbamoyloxy-1-(3-phenoxy-propyl)-trans-decahydroquinoline hydrochloride (axial form) | 252 ± 2 (ethyl acetate/methanol) |

-continued

| Compound | M.P. °C. |
|---|---|
| 1-[3-(4-Bromo-phenoxy)-propyl]-4-carbamoyloxy-trans-decahydroquinoline hydrochloride (axial form) | 257 ± 2 (methanol) |
| 4-Carbamoyloxy-1-[3-(4-chloro-phenoxy)-propyl]-trans-decahydroquinoline hydrochloride (axial form) | 236 ± 1 (methanol) |
| 4-Carbamoyloxy-1-[3-(4-methyl-phenoxy)-propyl]-trans-decahydroquinoline hydrochloride (axial form) | 244 ± 2 (methanol) |
| 4-Carbamoyloxy-1-[3-(4-methoxy-phenoxy)-propyl]-trans-decahydroquinoline hydrochloride (axial form) | 240 ± 2 (methanol) |
| 1-[3-(4-Acetyl-phenoxy)-propyl]-4-carbamoyloxy-trans-decahydroquinoline hydrochloride (axial form) | 254 ± 2 (ethyl acetate/ methanol) |
| 4-Carbamoyloxy-1-[3-(4-cyano-phenoxy)-propyl]-trans-decahydroquinoline hydrochloride (axial form) | 162 ± 1 (methanol) |
| 4-Carbamoyloxy-1-[3-(1-naphthyloxy)-propyl]-trans-decahydroquinoline hydrochloride (axial form) | 259 ± 1 (acetone) |
| 4-Carbamoyloxy-1-[3-(2-naphthyloxy)-propyl]-trans-decahydroquinoline hydrochloride (axial form) | >260 (acetone) |
| 4-Carbamoyloxy-1-[3-(4-fluoro-phenylthio)-propyl]-trans-decahydroquinoline hydrochloride (axial form) | 215 ± 1 (ethyl acetate/ methanol) |
| 1-[3-(4-Fluoro-phenoxy)-propyl]-4-(N-methylcarbamoyloxy)-trans-decahydroquinoline hydrochloride (axial form) | 220 ± 1 (methanol) |
| 4-(N-Ethylcarbamoyloxy)-1-[3-(4-fluoro-phenoxy)-propyl]-trans-decahydroquinoline hydrochloride (axial form) | 174 ± 1 (acetone) |
| 1-[3-(4-Fluoro-phenoxy)-propyl]-4-(N-n-propyl-carbamoyloxy)-trans-decahydroquinoline hydrochloride (axial form) | 159 ± 1 (acetone) |
| 4-(N-n-butylcarbamoyloxy)-1-[3-(4-fluoro-phenoxy)-propyl]-trans-decahydroquinoline hydrochloride (axial form) | 140 ± 1 (acetone) |
| 1-[3-(4-Fluoro-phenoxy)-propyl]-4-(N-phenylcarbamoyloxy)-trans-decahydroquinoline hydrochloride (axial form) | 219 ± 1 (ethyl acetate/ methanol) |
| 4-[(4-Bromo-phenyl)-carbamoyloxy]-[1-3-(4-fluoro-phenoxy)-propyl]-trans-decahydroquinoline hydrochloride (axial form) | 173 ± 1 (ethyl acetate) |
| 4-[3-(Chloro-4-methyl-phenyl)-carbamoyloxy]-1-[3-(4-fluoro-phenoxy)-propyl]-trans-decahydroquinoline hydrochloride (axial form) | 176 ± 1 (ethyl acetate) |
| 1-[3-(4-Acetyl-2-methoxy-phenoxy)-propyl]-4-carbamoyloxy-trans-decahydroquinoline hydrochloride (axial form) | 239 ± 1 (ethyl acetate/ methanol) |
| 1-[3-(4-Acetyl-2-methoxy-phenoxy)-propyl]-4-[4-(bromo-phenyl)-carbamoyloxy]-trans-decahydroquinoline hydrochloride (axial form) | 160 ± 1 (ethyl acetate/ methanol) |
| 4-Carbamoyloxy-1-[2-(2,6-dichloro-phenoxy)-ethyl]-trans-decahydroquinoline hydrochloride (axial form) | >260 (acetone) |
| 4-Carbamoyloxy-1-[2-(2-cyano-phenoxy)-ethyl]-trans-decahydroquinoline hydrochloride (axial form) | 206 ± 1 (acetone) |
| 4-Carbamoyloxy-1-[2-(2-methoxy-phenoxy)-ethyl]-trans-decahydroquinoline hydrochloride (axial form) | 226 ± 1 (ethyl acetate/ methanol) |
| 4-Carbamoyloxy-1-[2-(4-fluoro-phenoxy)-ethyl]-trans-decahydroquinoline hydrochloride (axial form) | 223 ± 1 (ethyl acetate/ methanol) |
| 1-[2-(4-Bromo-phenoxy)-ethyl]-4 carbamoyloxy-trans-decahydroquinoline hydrochloride (axial form) | ± 250 (methanol) |
| 4-Carbamoyloxy-1-[2-(1-naphthyloxy)-ethyl]-trans-decahydroquinoline hydrochloride (axial form) | 185 (methanol/ water/ ethyl acetate) |
| 4-Carbamoyloxy-1-[2-(2-naphthyloxy)-ethyl]-trans-decahydroquinoline hydrochloride (axial form) | >260 (methanol/ water/ ethyl acetate) |
| 4-Carbamoyloxy-1-[3-(4-fluoro-phenoxy)-propyl]-trans-decahydroquinoline hydrochloride (equatorial form) | 211 ± 1 (ethyl acetate/ methanol) |
| 4-[(4-Bromo-phenyl)-carbamoyloxy]-1-[3-(4-fluoro-phenoxy)-propyl]-trans-decahydroquinoline hydrochloride (equatorial form) | 241 ± 1 (ethyl acetate/ methanol) |
| 4-[(3-Chloro-4-methyl-phenyl)-carbamoyloxy]-1-[3-(4-fluoro-phenoxy)-propyl]-trans-decahydroquinoline hydrochloride (equatorial form) | 229 ± 1 (ethyl acetate/ methanol) |

EXAMPLE 3

4-Carbamoyloxy-1-[3-(4-fluoro-phenoxy)-propyl]-trans-decahydroquinoline methanesulphonate (axial form)

To a solution in 30 ml of acetone of 4 g (0.0114 mol) of 4-carbamoyloxy-1-[3-(4-fluoro-phenoxy)-propyl]-trans-decahydroquinoline (axial form) prepared as described in Example 2, was added the stoechiometric quantity of methanesulphonic acid from a 70%-aqueous solution of this acid dissolved in 30 ml of 2-propanol.

The reaction mixture was evaporated to dryness and the water was eliminated by means of several azeotropic distillations with toluene. The oily residue was then dissolved in ethyl acetate and allowed to cristallize. After filtration, the filter was washed with ethyl acetate.

In this manner, 3 g of 4-carbamoyloxy-1-[3-(4-fluoro-phenoxy)-propyl]-trans-decahydroquinoline methanesulphonate (axial form) were obtained.

EXAMPLE 4

4-Carbamoyloxy-1-[3-(4-fluoro-phenoxy)-propyl]-trans-decahydroquinoline hydrochloride (axial form)

(a)
1-[3-(4-Fluoro-phenoxy)-propyl]-4-hydroxy-trans-decahydroquinoline (axial form)

A mixture of 12.5 g (0.08 mol) of 4-hydroxy-trans-decahydroquinoline (axial form), 19 g (0.082 mol) of 1-(3-bromo-propoxy)-4-fluoro-benzene and 9 g of sodium hydrogenocarbonate in 100 ml of 1-butanol was heated to reflux for 48 hours with azeotropic elimination of the water formed. The subsequent working conditions were identical to those described in Example 1.

In this manner, 18.5 g of 1-[3-(4-fluoro-phenoxy)-propyl]-4-hydroxy-trans-decahydroquinoline (axial form) were isolated in free base form.
Yield: 76%
M.P.: 95±1° C.

(b)
4-Carbamoyloxy-1-[3-(4-fluoro-phenoxy)-propyl]-trans-decahydroquinoline hydrochloride (axial form)

While stirring, 1.2 g (0.0075 mol) of phenyl chloroformiate was added dropwise to a solution of 1.5 g (0.005 mol) of 1-[3-(4-fluoro-phenoxy)-propyl]-4-hydroxy-trans-decahydroquinoline (axial form) in 0.9 ml of pyridine and 15 ml of benzene, care being taken to maintain the temperature between 0° and 20° C. during the operation. Stirring was maintained for 48 hours at room-temperature and then the reaction medium was poured into an aqueous solution of sodium carbonate. After extraction with benzene, the organic phase was decanted out. The solvent was evaporated off and the residue was taken up in 10 ml of methanol saturated in ammonia.

After 48 hours at room-temperature, the solvent was evaporated off, the residue was dissolved in benzene and this solution was washed first with water, then with a diluted sodium hydroxide solution and finally with water. The solvent was evaporated off and the residue was taken up in ethyl acetate.

The subsequent working conditions were identical to those described in Example 1.

In this manner, 1.2 g of 4-carbamoyloxy-1-[3-(4-fluoro-phenoxy)-propyl]-trans-decahydroquinoline hydrochloride (axial form) was obtained.
M.P.: 238±1° C.

EXAMPLE 5

In accordance with known pharmaceutical techniques, a soft-gelatin capsule was prepared by associating the following ingredients:

| Ingredients | mg |
| --- | --- |
| 4-Carbamoyloxy-1-[3-(4-fluoro-phenoxy)-propyl]-trans-decahydroquinoline hydrochloride (axial form) | 100 |
| Corn starch | 384 |
| Talc | 10 |
| Colloidal silica | 6 |
| | 500 |

EXAMPLE 6

In accordance with known pharmaceutical techniques, an uncoated tablet as well as coated tablets were prepared by granulating and compressing the following ingredients:

(a) Uncoated tablet

| Ingredients | mg |
| --- | --- |
| 4-Carbamoyloxy-1-[3-(4-fluoro-phenoxy)-propyl]-trans-decahydroquinoline hydrochloride (axial form) | 100 |
| Milk sugar | 128 |
| Polyvinylpyrrolidone | 12 |
| Sodium carboxymethylstarch | 48 |
| Magnesium stearate | 8 |
| Talc | 4 |
| | 300 |

(b) Coated tablet

A coated tablet was prepared from the above-described core by adding the varnish hereunder:

| | | |
| --- | --- | --- |
| Cationic polyacrylate | ±9 | mg |
| Polyethyleneglycol 6000 | ±4 | mg |
| Talc | ±40 | mg |
| Hydroxypropylcellulose | ±0.4 | mg |
| Titanium oxide | ±26.6 | mg |
| | ±80 | mg |

(c) Entero-soluble coated tablet

An enteric coated tablet was prepared from the above-exemplified coated tablet by adding the enteric coating given hereunder:

| | |
| --- | --- |
| Cellulose acetophthalate | 40 mg |
| Diethylphthalate | 10 mg |

EXAMPLE 7

In accordance with known pharmaceutical techniques, an injectable solution was prepared from the following ingredients:

| Ingredients | mg |
| --- | --- |
| 4-Carbamoyloxy-1-[3-(4-fluoro-phenoxy)-propyl]-trans-decahydroquinoline hydrochloride (axial form) | 200 |
| Mannitol | 800 |
| Distilled water s.a. for | 20 ml |

We claim:
1. A decahydroquinolinol compound of the formula:

$$\text{structure with } O-C(=O)-NHR^1 \text{ group on decahydroquinoline ring, N-}(CH_2)_n-X-Ar$$

and pharmaceutically acceptable acid addition salts thereof, in which $R^1$ represents hydrogen, methyl, ethyl, n-propyl, n-butyl or 3-chloro-4-methylphenyl, Ar represents 4-fluorophenyl, 4-bromophenyl or 4-cyanophenyl, X represents oxygen, and n is 3.

2. Decahydroquinolinol derivatives according to claim 1 in the form of axial epimers.

3. Decahydroquinolinol derivatives according to claim 1 in the form of equatorial epimers.

4. 4-Carbamoyloxy-1-[3-(4-fluoro-phenoxy)-propyl]-trans-decahydroquinoline (axial form) and pharmaceutically acceptable acid addition salts thereof.

5. 1-[3-(4-Bromo-phenoxy)-propyl]-4-carbamoyloxy-trans-decahydroquinoline (axial form) and pharmaceutically acceptable acid addition salts thereof.

6. 4-Carbamoyloxy-1-[3-(4-cyano-phenoxy)-propyl]-trans-decahydroquinoline (axial form) and pharmaceutically acceptable acid addition salts thereof.

7. 1-[3-(4-Fluoro-phenoxy)-propyl]-4-(N-methylcarbamoyloxy)-trans-decahydroquinoline (axial form) and pharmaceutically acceptable acid addition salts thereof.

8. 4-(N-Ethylcarbamoyloxy)-1-[3-(4-fluoro-phenoxy)-propyl]-trans-decahydroquinoline (axial form) and pharmaceutically acceptable acid addition salts thereof.

9. 1-[3-(4-Fluoro-phenoxy)-propyl]-4-(N-n-propylcarbamoyloxy)-trans-decahydroquinoline (axial form) and pharmaceutically acceptable acid addition salts thereof.

10. 4-(N-n-Butylcarbamoyloxy)-1-[3-(4-fluoro-phenoxy)-propyl]-trans-decahydroquinoline (axial form) and pharmaceutically acceptable acid addition salts thereof.

11. 4-Carbamoyloxy-1-[3-(4-fluoro-phenoxy)-propyl]-trans-decahydroquinoline (equatorial form) and pharmaceutically acceptable acid addition salts thereof.

12. 4-[(3-Chloro-4-methyl-phenyl)-carbamoyloxy]-1-[3-(4-fluoro-phenoxy)-propyl]-trans-decahydroquinoline (equatorial form) and pharmaceutically acceptable acid addition salts thereof.

13. Decahydroquinolinol derivatives according to any of claims 1 to 10 or 11 to 12 wherein the pharmaceutically acceptable acid addition salt is the hydrochloride or the methanesulphonate.

14. A pharmaceutical or veterinary composition for treatment of cardiac arrhythmias comprising, as essential active ingredient, at least one decahydroquinolinol compound according to claim 1, in association with a pharmaceutical carrier or excipient.

15. Method of treating cardiac arrhythmias of various origins and in particular arrhythmias due to myocardial infarction in a host in need of such treatment which method comprises the administration to said host of an effective dose of at least one decahydroquinolinol derivative according to claim 1.

16. Method according to claim 15 wherein the effective dose is 100 to 200 mg by oral route to a human being weighing 60 kgs.

17. Method of inducing local anaesthesia in a host in need thereof which method comprises the administration to said host of an effective dose of at least one decahydroquinolinol derivative according to claim 1.

* * * * *